United States Patent [19]

Cooper et al.

[11] Patent Number: 5,376,398

[45] Date of Patent: Dec. 27, 1994

[54] REDUCED CALORIE FOOD COMPOSITIONS CONTAINING FATTY ACID-ESTERIFIED POLYTETRAMETHYLENE ETHER GLYCOL FAT SUBSTITUTES

[75] Inventors: Charles F. Cooper, Paoli; Stephen D. Harper, West Chester, both of Pa.

[73] Assignees: Arco Chemical Technology, L.P., Wilmington, Del.; CPC International Inc., Englewood Cliffs, N.J.

[21] Appl. No.: 141,913

[22] Filed: Oct. 22, 1993

[51] Int. Cl.$^5$ .............................................. A23D 9/00
[52] U.S. Cl. ...................................... 426/611; 426/804
[58] Field of Search ................................ 426/804, 611

[56] References Cited

U.S. PATENT DOCUMENTS

| | | | |
|---|---|---|---|
| 4,464,182 | 8/1984 | Tack et al. | 44/62 |
| 4,849,242 | 7/1989 | Kershner | 426/601 |
| 4,861,613 | 8/1989 | White et al. | 426/611 |
| 5,077,073 | 12/1991 | Ennis et al. | 426/531 |

FOREIGN PATENT DOCUMENTS

| | | |
|---|---|---|
| 0415636 | 3/1991 | European Pat. Off. |
| 0433016 | 6/1991 | European Pat. Off. |
| 0481523 | 4/1992 | European Pat. Off. |
| 207070 | 2/1984 | Germany |
| WO9110368 | 7/1991 | WIPO |
| WO9201386 | 2/1992 | WIPO |

OTHER PUBLICATIONS

Encyclopedia of Polymer Science and Engineering vol. 16 Tetrahydrofuran Polymers pp. 649–681 John Wiley & Sons New York.

Aust, L., G. Mieth, J. Proll, A. Elsner, H. Behrens, W. Gerhardt, J. Bruckner, and R. Noack, "Orientational Studies on the Metabolism of Various Acaloric Compounds with Fat-Like Properties In the Rat", Die Nahrung, vol. 32, No. 1, pp. 49–57, 1988.

Mieth, G., A. Elsner, J. Bruckner, A. Weiss, and H. Behrens; Acaloric Compounds with Fat-Like Functional Properties (Pseudofats), Die Nahdungen, vol. 27, No. 9, pp. 853–876, 1983.

*Primary Examiner*—Carolyn Paden
*Attorney, Agent, or Firm*—Stephen D. Harper

[57] ABSTRACT

Fatty acid-esterified polytetramethylene ether glycols are useful as reduced calorie fat substitutes in food composition. Fat mimetics of this type have good organoleptic properties as well as high resistance to thermal and oxidative degradation, making them especially suitable for the preparation of fried and baked foods. In certain embodiments, fat substitutes having a high solids content at room or body temperature may be readily obtained without the use of high proportions of long chain saturated fatty acids.

21 Claims, No Drawings

REDUCED CALORIE FOOD COMPOSITIONS CONTAINING FATTY ACID-ESTERIFIED POLYTETRAMETHYLENE ETHER GLYCOL FAT SUBSTITUTES

FIELD OF THE INVENTION

This invention relates to food compositions utilizing a polytetramethylene ether glycol esterified with a fatty acid entity to replace, in whole or in part, conventional high calorie edible lipids. The fatty acid-esterified polytetramethylene ether glycol fat mimetics are surprisingly resistant to lipase-catalyzed hydrolysis, despite the primary structure of the ester linkages contained therein. At the same time, however, sufficient partial digestion takes place upon consumption so as to alleviate the problems with anal oil leakage often encountered with synthetic fat substitutes.

BACKGROUND OF THE INVENTION

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from these fat substitutes is considerably reduced as compared to common vegetable oils, animal fats, and other lipids. Such substances thus may be utilized in the preparation of reduced calorie food compositions useful in the control of body weight.

U.S. Pat. No. 4,861,613 describes one class of particularly useful fat substitutes wherein a polyol such as glycerin is alkoxylated with an epoxide such as propylene oxide under basic conditions and then esterified with any of a number of fatty acids to form an esterified epoxide-extended polyol. These substances have the physical and organoleptic properties of conventional triglyceride lipids, yet are significantly lower in available calories owing to their pronounced resistance towards pancreatic lipase-catalyzed hydrolysis.

Unfortunately, as a consequence of their hydrolytic stability, low digestibility, and lipophilic character the esterified epoxide-extended polyols described in U.S. Pat. No. 4,861,613 which are fully liquid at body temperature may tend to cause certain undesirable gastrointestinal side effects when consumed at high levels in the diet. That is, since such esterified alkoxylated polyols are not readily broken down into simpler substances upon ingestion, they retain their oily, fat-like character and pass through the digestive tract in substantially unaltered form. Problems with leakage of the fat substitute through the anal sphincter and separation of the fat substitute as an oil from the excreted fecal matter can occur as a result of the digestion-resistant character of the fat substitute. Other fat substitutes which are similarly resistant towards digestion are known to produce the same sort of gastrointestinal side effects. Examples include sucrose polyester which is esterified with up to 8 fatty acid groups; see U.S. Pat. Nos. 3,954,976, 4,005,195, 4,005,196, and 5,006,360. Obviously, such problems will greatly limit the maximum level of these substances which can be tolerated in various food compositions, thereby constraining the amount of conventional triglyceride and the number of calories which can be removed from certain foods.

One solution to the problem of anal oil leakage is taught in U.S. patent application Ser. No. 07/886,538, filed May 20, 1992, which discloses esterified propoxylated glycerin fat substitute compositions containing relatively large proportions of $C_{20}$-$C_{24}$ saturated fatty acid acyl groups and having a solid fat index at 27° C. above 30. Although such substances are effective in lessening the severity of gastrointestinalside effects, they are significantly more difficult and costly to synthesize than analogous esterified propoxylated glycerins made from shorter chain and/or unsaturated fatty acids. It would thus be advantageous to develop leakage-resistant fat mimetics which are available at lower cost.

An important practical requirement for a fat replacement is sufficient resistance to oxidative and thermal degradation at elevated temperatures to permit the use of the fat mimetic in deep fat frying applications and other cooking applications. Among the problems which can result if a lipid is exposed to high temperatures for an extended period of time are discoloration, smoking, generation of volatile decomposition products, development of off-flavors and unacceptable odor, thickening or gelling due to cross-linking or polymer formation, production of toxic by-products, and so forth. Certain fat substitutes such as those derived from proteinaceous materials are not suitable for use in cooking since their fat-like properties are destroyed upon exposure to heat. Other fat substitutes, such as the esterified epoxide-extended polyols described in U.S. Pat. No. 4,861,613, are considerably more stable and thus are generally suitable for use in the preparation of cooked food. However, such compounds are still somewhat susceptible to degradation under severe conditions owing to the presence of readily-abstractable tertiary hydrogens in the poly(oxypropylene) segments of these materials. Thus, it would be highly desirable to obtain fat mimetics which are even more resistant to heat than esterified epoxide-extended polyols without sacrificing the desirable low digestibility and fat-like properties exhibited by such substances.

A method of improving the stability of esterified epoxide-extended polyol fat substitutes is described in U.S. patent application Ser. Nos. 07/633,814, filed Dec. 27, 1990 and 07/886,583, filed May 20, 1992, wherein the oxyalkylene repeating units found in such substances are partially replaced with ring-opened oxolane units. These applications stress, however, the criticality of retaining $C_3$ or higher epoxide-derived oxyalkylene repeating units adjacent to the fatty acid acyl groups in order to provide resistance to lipase-catalyzed hydrolysis. According to these applications, the presence of primary ester linkages, such as those obtained by direct reaction of a polytetramethylene glycol with a fatty acid, would increase the available caloric content to an undesirable extent since such linkages would be as susceptible to digestion as the ester linkages in a conventional fatty acid triglyceride (i.e., a fatty acid triester of glycerin).

Despite the considerable research performed in the last two decades in the field of synthetic fat substitutes, an understanding of the precise relationship between chemical structure and digestibility is still lacking and the field remains a highly uncertain and unpredictable art. The technical literature related to fat substitutes is replete with conflicting observations and findings which cannot easily be reconciled or explained. For example, U.S. Pat. No. 4,861,613 (White et al.) teaches that a polyol such as glycerin should be reacted (epoxylated) with a quantity of a $C_3$–$C_6$ epoxide sufficient to convert greater than 95% of the primary hydroxyl groups of the polyol to secondary or tertiary hydroxyl groups prior to esterification with a fatty acid in order to obtain a low calorie fat substitute. The low digestibility of the final esterified epoxide-extended polyol was attributed primarily to the presence of secondary and tertiary ester linkages since substances with lower degrees of alkoxylation were found to be susceptible to lipase-catalyzed hydrolysis.

In contrast, U.S. Pat. No. 4,849,242 (Kershner) teaches the preparation of reduced calorie food compositions containing oil-like polymer fatty acid esters having the property of being substantially hydrolyzed during the process of intestinal digestion into a mixture of fatty acids and a non-caloric water-soluble or water-dispersible polymeric alcohol. Fatty acid esters of water-soluble polyoxyalkylenes are said to be particularly useful for this purpose. Kershner teaches that polyoxyethylenes, polyoxypropylenes, and polyoxybutylenes are all equally well-suited for use as the polyoxyalkylene starting material, thus implying that the fatty acid esters of such substances will be readily hydrolyzed upon ingestion. Thus, no distinction between primary and secondary ester linkages in terms of their susceptibility to enzyme-catalyzed hydrolysis was recognized.

Quite different conclusions were reached in U.S. Pat. Nos. 5,059,443 (Ennis et al.) and 5,077,073 (Ennis et al.) which respectively describe the use of esterified alkoxylated alkyl glycosides and esterified alkoxylated sugars and sugar alcohols as low calorie fat substitutes. The rate of hydrolysis of the ester bonds was found to be quite low for these substances relative to triglycerides. Moreover, the resistance to hydrolysis was reported to be approximately equally high regardless of whether ethylene oxide or propylene oxide was utilized in the alkoxylation. That is, no significant difference in reactivity was observed between substances with primary ester linkages (derived from ethylene oxide) and substances with secondary ester linkages (derived from propylene oxide).

The preparation of polytetramethylene ether glycols esterified with behenic acid and the use of such substances as flow improver additives for distillate fuels has been previously described in U.S. Pat. No. 4,464,182 (Tack et al., Examples 17 and 22). This publication does not suggest that these substances could be employed as food additives.

SUMMARY OF THE INVENTION

We have now found that polytetramethylene ether glycols esterified with fatty acids are useful as low calorie fat substitutes and mimetics, contrary to earlier expectations. Despite the fact that such substances predominantly or exclusively contain primary rather than secondary or tertiary ester linkages, they have substantially reduced caloric content relative to natural fats and oils. As compared to esterified epoxide-extended polyols prepared using propylene oxide, the fat substitutes used in the composition of this invention have improved oxidative and thermal stability and may be more readily obtained in solid or partially solid form.

This invention provides a fat component useful for preparing a reduced calorie food product wherein said fat component comprises an edible triglyceride and a polytetramethylene ether glycol esterified with a fatty acid entity. Also provided is a reduced calorie food product comprised of at least one non-fat ingredient and a fat component wherein such fat component comprises, in whole or in part, a polytetramethylene ether glycol esterified with a fatty acid entity. Also furnished by this invention is a method of reducing calories in a food product comprised of a fat component, where the method comprises replacing an effective portion of the fat component with a polytetramethylene ether glycol esterified with a fatty acid entity.

DETAILED DESCRIPTION OF THE INVENTION

The fatty acid-esterified polytetramethylene ether glycols (hereinafter sometimes referred to as "esterified PTMEGs") used as reduced calorie fat substitutes in the compositions of the invention are organic compounds comprised of two types of covalently bonded moieties, namely, (i) a plurality (i.e., 2 or more) of oxytetramethylene repeating units having the structure —$CH_2CH_2CH_2CH_2$—O— and (2) acyl groups derived from a fatty acid or fatty acid equivalent such as a halide, anhydride, or ester (hereinafter sometimes referred to collectively as "fatty acid entity", meaning any long chain carboxyl-containing substance capable of participating in an esterification reaction with a polytetramethylene ether glycol). In order to minimize the amount of direct absorption through the intestinal wall when consumed as part of a food product, which can result in a higher than desired caloric availability, the molecular weight of the esterified PTMEG should be at least 600 and more preferably is from 900 to 3700.

The polytetramethylene ether glycol selected for use may preferably have a molecular weight prior to esterification of from 160 to 5000 and a functionality (i.e., number of hydroxyl groups per molecule) of from 1 to 8, but more preferably has a molecular weight of from 400 to 3000 and a functionality of 2. Such materials are well-known in the art and may be readily obtained as described, for example, in Dreyfuss et al., "Tetrahydrofuran Polymers", *Encyclopedia of Polymer Science and Technology*, Vol. 16, Wiley-Interscience, pp. 649–681 (1989). Polytetramethylene ether glycols suitable for use in preparing the fatty acid-esterified fat substitutes utilized in the instant invention are also available commercially from a number of sources including BASF Corporation ("POLYTHF"), E. I. du Pont de Nemours ("TERETHANE"), and QO Chemicals ("POLYMEG"). The polytetramethylene ether glycol may, if desired, contain minor amounts (e.g., 1 to 20 weight percent) of oxyethylene and/or oxypropylene repeating units in addition to the oxytetramethylene repeating units, preferably incorporated in a random manner within the polytetramethylene ether glycol rather than as end-caps.

In a preferred embodiment, the esterified PTMEG has the general structure

wherein n is from 2 to 55 (more preferably, from 4 to 40) and $R^1$ and $R^2$ are the same or different and are $C_5$–$C_{23}$ olefinic (including mono-unsaturated and polyunsaturated) or paraffinic (saturated) groups. It has been found that the melting point of the esterified PTMEG generally increases as the value of n (i.e., the number of oxytetramethylene repeating units) is increased. This result was surprising in view of the fact that in the analogous esterified epoxide-extended polyols prepared using propylene oxide as the epoxide, melting points typically decrease with an increasing degree of propoxylation. An advantage of the present invention is that relatively high melting fat substitutes may be obtained without the use of high proportions of long chain (i.e., $C_{18}$ and higher) saturated fatty acids. A relatively hard fat substitute thus can be produced which incorporates substantial amounts of short chain and/or unsaturated fatty acids. The use of polytetramethylene ether glycol starting materials having a molecular weight of at least 1000 is desirable where a higher melting esterified PTMEG is desired.

The acyl groups in the esterified PTMEG are preferably derived from a fatty acid, although any suitable fatty acid equivalent could also be utilized. The fatty acid may be linear or branched. Saturated as well as unsaturated fatty acids and their equivalents are suitable for use. Preferably, monocarboxylic acids (i.e., fatty acids containing only one carboxylic acid functionality) are employed. Such fatty acids and their equivalents (e.g., fatty acid esters, fatty acid halides, fatty acid anhydrides) are readily available at low cost from natural sources such as triglycerides. Any of the known natural or synthetic fatty acids may be used, including, for example, caprylic, capric, caproic, pelargonic, gadoleic, erucic, arachidonic, lauric, myristic, myristoleic, stearic, isostearic, palmitic, palmitoleic, rincinoleic, linoleic, linolenic, elaeostearic, arachidic, heneicosanoic, lignoceric, behenic, erucic, oleic, and heptadecanoic acid or mixtures thereof. The physical properties of the esterified PTMEG may be varied as desired by changing the length and structure of the fatty acid-derived acyl groups; products which are liquid oils, fats, greases, or solid waxes may thus be obtained. Mixtures of different fatty acids may advantageously be used, including those mixtures obtained by splitting (hydrolysis) of natural or modified triglycerides such as rapeseed oil, tallow, soybean oil, cottonseed oil, coconut oil, palm kernel oil, babassu oil, corn oil, fish oil, lard, olive oil, palm oil, peanut oil, safflower seed oil, sesame seed oil, jojoba oil, and sunflower seed oil or fully or partially hydrogenated derivatives thereof.

The esterified PTMEGs employed in preparing the compositions of this invention are characterized by an exceptionally high proportion of primary ester linkages. "Primary ester linkage" in this context means that the carbon atom attached to the oxygen atom adjacent to carbonyl bears two hydrogen atoms. In a secondary ester linkage, the analogous carbon atom bears only one hydrogen atom. In preferred embodiments of the invention, essentially 100% of the ester linkages present in the esterified PTMEG are primary in structure. Despite this structural feature, the esterified PTMEGs impart considerably fewer available calories to a food product than an equivalent amount of a triglyceride such as corn oil or soybean oil. Preferably, the esterified PTMEG has a caloric content which is less than 50% (more preferably, less than 33%) of the caloric content of a natural triglyceride such as olive oil. The caloric content thus desirably is less than about 3 kilocalories per gram. The esterified PTMEG, despite containing a very high proportion of primary ester linkages, typically displays in-vitro normalized hydrolysis rates of less than 20% compared to an olive oil standard using porcine pancreatic lipase as catalyst. Normalized hydrolysis rates of less than 10% relative to olive oil are also readily attainable. This result was quite unexpected in view of the teaching of U.S. Pat. No. 4,861,613 that hydrolysis resistance of this magnitude in an esterified alkoxylated polyol is only achieved when the primary ester content is less than 5%. The high resistance to lipase-catalyzed hydrolysis was also surprising in view of the fact that 2 out of the 3 ester linkages in a fully digestible fatty acid triglyceride are primary in structure.

At the same time, however, the esterified PTMEG's of this invention do exhibit a measurable (albeit low) rate of hydrolysis indicating that partial breakdown of the fat substitute will take place during the 12–48 hour period of transit through the human digestive system. The susceptibility of the ester bonds incorporated in the esterified PTMEG towards cleavage thus has been advantageously adjusted to a level intermediate between that of esterified propoxylated glycerin and a natural fat or oil. The esterified PTMEG thus simultaneously not only displays a considerable reduction in effective caloric value as compared to the latter class of food ingredients, but also is in part converted by digestive processes to a product which is less oil-like in nature. The product of such a controlled digestive process may have decreased hydrophobicity, and thus greater hydrophilicity, and/or a higher melting point relative to the parent esterified PTMEG. Such a product will tend to have not only decreased oiliness, but may also function as an emulsifier or binder capable of emulsifying, solidifying, or binding any undigested fat substitute or oil-like digestive by-product. Thus, the fat substitutes of this invention can be selected such that they will be less prone to exit the gastrointestinal tract as a persistent oil as compared to certain substances taught as fat substitutes in the prior art such as the esterified epoxide-extended polyols taught in U.S. Pat. No. 4,861,613. Thus, in a preferred embodiment of this invention, the esterified PTMEG will have a normalized hydrolysis rate of greater than 1% but less than 10% relative to olive oil.

In certain desirable embodiments of the invention, the structure of the esterified PTMEG is selected such that the fat substitute is fully liquid or has a relatively low solid fat index (e.g., 0 to 50) at body temperature (37° C.). The incorporation of short chain (i.e., less than $C_{20}$), unsaturated (e.g., oleic, linoleic, linolenic), or branched chain (e.g., isostearic) fatty acids generally tends to depress the melting range of the unesterified PTMEG. The partial hydrolysis of the esterified PTMEG which takes place upon ingestion will generate partially esterified or unesterified PTMEG, which will be resistant to further metabolic breakdown and which will also typically have a higher solid fat index than the original esterified PTMEG. The increase in solid fat content (generally, at least about 30) helps to minimize problems with so-called anal oil leakage and separation of the fat substitute as an oil from the excreted fecal matter. This invention thus enables the preparation of fat substitutes which have a desirable non-waxy mouthfeel and consistency, yet do not exhibit certain of the undesirable side effects commonly observed in reduced calorie oils.

The esterified PTMEG's employed in this invention may be prepared by any appropriate synthetic method. One such method involves first polymerizing tetrahydrofuran under cationic conditions so as to ring-open the tetrahydrofuran and form a polytetramethylene ether glycol, and then esterifying the polytetramethylene ether glycol by reacting with one or more fatty acids or fatty acid derivatives. Alternatively, an oligomeric condensate of 1,4-butanediol may be used as a starting material. It is also possible to obtain esterified PTMEG directly by reacting tetrahydrofuran and a fatty acid anhydride in the presence of a suitable cationic polymerization catalyst such as an acid-activated bleaching earth as described, for example, in U.S. Pat. Nos. 4,243,799 and 4,803,299.

The esterification of the polytetramethylene ether glycol may be accomplished using any suitable method known for synthetic transformations of this type. For example, a fatty acid or mixture of fatty acids may be reacted with the polytetramethylene ether glycol to yield the esterified PTMEG product and water as a co-product. A catalyst may be used to accelerate the reaction, preferably an acidic catalyst such as a mineral acid (sulfuric acid, for example) or a sulphonic acid (p-toluene sulphonic acid, for example). Catalysts which may tend to depolymerize the polytetramethylene ether glycol should be avoided, however. The water co-product may be removed continuously from the reaction mixture using a method such as azeotropic distillation, sparging, or vacuum distillation in order to drive the reaction to completion. Alternatively, a transesterification reaction may be employed wherein a fatty acid ester

or mixture of fatty acid esters is reacted with the PTMEG. Preferably, the fatty acid ester is an ester of a $C_1$-$C_4$ alcohol such as methanol or ethanol. The low boiling alcohol formed as a co-product may be removed from the transesterification reaction mixture in order to drive the equilibrium reaction to completion in the desired direction. A catalyst such as an acidic or basic catalyst may be used in the transesterification. In yet another approach, the PTMEG may be reacted with an acid halide derivative of one or more fatty acids

wherein X=Cl, Br, etc.,]. Alternatively, a fatty acid anhydride such as stearic anhydride could be utilized. Methods of accomplishing esterification of alcohols using various fatty acid-based reactants are well known in the field and are described, for example, in Markley, "Esters and Esterification," in *Fatty Acids*, Markley, ed., 2nd edition, Part 2, Chapter IX, pp. 757–984 (1961).

The polytetramethylene ether glycol and the fatty acid compound are reacted for a time and at a temperature sufficient to accomplish esterification of the hydroxyl groups of the PTMEG. It is not necessary to achieve complete esterification in the esterified PTMEG's employed in the compositions of this invention. In fact, it may be desirable to leave some portion of the hydroxyl groups unesterified to vary certain properties of the fat mimetic such as its propensity for promoting anal oil leakage. Preferably, however, at least about 90% of the hydroxyl groups in the PTMEG are esterified. The optimum reaction conditions will vary somewhat depending upon the particular type of fatty acid entity used. If a fatty acid or fatty acid ester is utilized, the reaction temperature is preferably from about 100° C. to 350° C.; reaction times of from about 1 to 48 hours are generally sufficient to effect substantially complete esterification of the hydroxyl groups. When the fatty acid entity is a fatty acid halide, somewhat lower reaction temperatures (e.g., about 25° C. to 125° C.) are sufficient, particularly if a tertiary amine such as triethylamine is additionally present to take up the hydrogen halide generated during the esterification reaction. Reaction times of from about 1 to 48 hours are typically sufficient.

To accomplish substantially complete esterification of the PTMEG, at least about 1 (more preferably, at least about 1.1) equivalent of the fatty acid entity per equivalent of hydroxyl groups in the PTMEG are used. For reasons of economy, it is preferred to react not more than about 3 equivalents of fatty acid entity. Any excess fatty acid entity may be removed from the esterified PTMEG by an appropriate method such as vacuum steam stripping.

A reduced calorie esterified PTMEG fat substitute produced by the methods described hereinabove can be additionally purified or treated so as to render it more suitable for use in food compositions using any of the techniques known in the art for refining natural vegetable or animal lipids or other synthetic fat substitutes. Such techniques include, but are not limited to, degumming, bleaching, filtration, deodorization, hydrogenation, dewaxing, and the like. Various additives such as stabilizers, anti-oxidants (e.g., tocopherols, hindered phenols such as BHT, hydroquinones such as TBHQ), vitamins (e.g., fat-soluble vitamins such as vitamin A, D, E, and K) and so forth can also be incorporated into the esterified PTMEG.

It should be understood that by the nature of the chemical reactions used to prepare the esterified PTMEGs, the products obtained will typically be mixtures of individual compounds which have a range of molecular weights and which may contain structural isomers. It may be useful to deliberately blend individually prepared esterified PTMEGs having different molecular weights, different oxytetramethylene repeating unit contents, different functionality, and/or different acyl groups in order to obtain fat mimetics having certain desired properties.

The esterified PTMEGs may be used as partial or total (100%) replacements for triglyceride lipids in any edible fat-containing food composition. The amount of the fat mimetic employed is sufficient to effectively reduce the available calories of the food composition as compared to a food composition prepared using an equivalent amount (weight or volume) of a triglyceride lipid. Preferably, at least about 10 percent (more preferably, at least about 25 percent by weight) of the total fat-like component of the food composition is comprised of the esterified PTMEG.

The triglyceride admixed with the esterified PTMEG may be any of the known edible fatty acid triglycerides available from natural or synthetic sources. These edible fatty acid triglycerides include, but are not limited to, fats and oils such as tallow, soybean oil, cottonseed oil, coconut oil, palm kernel oil, corn oil, fish oil, lard, butterfat, olive oil, palm oil, peanut oil, safflower seed oil, cocoa butter, sesame seed oil, rapeseed oil, sunflower seed oil, as well as fully or partially hydrogenated derivatives and mixtures of these triglycerides. While the esterified PTMEG may be combined in any proportion with the triglyceride, weight ratios of from 5:95 to 95:5 are particularly advantageous. The triglyceride may be selected so as to impart a desirable caloric content, flavor, aroma, mouthfeel, thermal stability, viscosity, rheology (Newtonian or non-Newtonian) or other property to the blend and to the resulting food composition.

The physical, organoleptic, and physiological properties and characteristics of the esterified PTMEGs may be controlled as desired by varying the identities and relative proportions of the oxytetramethylene repeating units and fatty acids incorporated therein. The composition of the esterified PTMEGs may thus be readily altered so as to render the fat substitute completely liquid, completely solid, or partially liquid and partially solid at room temperature (i.e., the solid fat index may range from 0 to 100%). In certain preferred embodiments, the solid fat index at room temperature (21° C.) as measured by dilatometry is greater than 50. In other preferred embodiments, the solid fat index at 27° C. is greater than 30, more preferably greater than 40.

Certain relatively high-melting esterified PTMEGs within the scope of this invention may tend to have a waxy or gritty mouthfeel as a consequence of their high solids content at room or body temperature. To eliminate or minimize any such unpleasant organoleptic properties, the fat substitutes are preferably combined with one or more liquid triglyceride lipids. The lipid may be any of the fatty acid triglycerides discussed hereinabove provided it has a complete melting point of 37° C. (body temperature) or below (more preferably, a complete melting point of 25° C. or below). The esterified PTMEG is advantageously dispersed in the form of fine particles in a matrix of the liquid triglyceride lipid. Preferably, the particles have an average size of 25 microns or less (more preferably, 10 microns or less). The weight ratio of liquid triglyceride lipid to esterified PTMEG is desirably from about 0.5:1 to about 10:1 (more preferably from about 1.5:1 to about 4:1). To obtain dispersions of this type, the esterified PTMEG and liquid triglyceride lipid may be combined in slurry form and the resulting slurry subjected to milling. The temperature during the milling operation, which reduces the particle size of the esterified PTMEG to the desired level, should be maintained below (preferably, at least 15° F. below) the complete melting point of the esterified PTMEG (the minimum temperature at which it has a solid-fat index of 0).

The esterified PTMEG fat substitute can replace, in full or in part, a triglyceride lipid in a cooking oil, frying oil, salad oil, or shortening, for example. Additional uses include combining the esterified PTMEG with other foodstuff ingredients to form food products such as frozen desserts (e.g., sherbert, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels), fried foods (fried poultry, fritters, fried pies, fried vegetables such as french fried potatoes, fried fish), reformed and comminuted meats (lunch meats, sausage, hot dogs, hamburger), pet foods, meat and egg substitutes or extenders, whipped toppings, gravies and other sauces, frostings, fillings, icings, cocoa butter replacements or blends, candies and confectioneries (especially those normally containing fatty ingredients such as chocolate or peanut butter), soups, and dry baking mixes (for muffins, cakes, pancakes, waffles, brownies, and the like). Owing to the fat-like properties and stability of the esterified PTMEG, minimum reformulation of standard food compositions will generally be required. The viscosity, melting profile, yield point, hardness, thixotropic area, liquid/solid stability, solid fat index, rheology, plasticity, and other physical properties of the esterified PTMEG are preferably selected such that they mimic as closely as possible the analogous properties of the conventional triglyceride being replaced.

Illustrative ingredients (including both fatty food ingredients and non-fat food ingredients) which may be used in combination with the esterified PTMEG fat mimetics include carbohydrates (flour, starches, sugars, celluloses), edible lipids (triglycerides), proteins (from animal or vegetable sources), vitamins (including, but not limited to, fat soluble vitamins such as vitamin A, vitamin D, vitamin E, and vitamin K), antioxidants, emulsifiers (including, but not limited to, the emulsifiers listed as approved for food use in the United States Code of Federal Regulations), thickeners, preservatives, colorants, flavors, fragrances, sugar substitutes (saccharin, aspartame, sucralose, cyclamates, and the like), other fat substitutes or fat mimetics (for example, polyol polyesters such as sorbitol polyester and sucrose polyester, esterified alkoxylated polyols such as esterified propoxylated glycerin, or caprenin), bulking agents such as polydextrose, dietary fibers, water, milk, spices, eggs, and the like. Oil-in-water or water-in-oil emulsions can be readily prepared by combining water, the esterified PTMEG, and (optionally) other ingredients such as emulsifiers. The esterified PTMEGs are particularly suitable for the preparation of food compositions requiring exposure to elevated temperatures. Unlike other proposed fat substitutes such as proteinacious macrocolloids or certain polysaccharide-based substances requiring water to render them fat-like in texture, the fat mimetics of this invention are thermally stable and do not readily decompose or lose their fat-like properties when heated. The esterified PTMEGs have also been found to be more resistant to oxidative degradation under extreme conditions than fat substitutes prepared using 1,2-alkylene oxides such as propylene oxide. The fat mimetics thus may readily be utilized in deep fat frying applications to prepare fried foods such as savory snacks (e.g., potato chips), fried chicken, fried fish, french fries, and the like since they will function as effective heat transfer media (that is, they will transmit heat rapidly and uniformly to the food being fried and also provide crisping).

From the foregoing description, one skilled in the art can readily ascertain the essential characteristics of this invention and, make various changes and modifications of the invention to adapt it to various usages, conditions, and embodiments.

The following examples further illustrate the compositions of this invention, but are not limitative of the invention in any manner whatsoever.

EXAMPLES 1-3

A fatty acid-esterified polytetramethylene ether glycol was prepared by combining 650 parts of a 650 molecular weight polytetramethylene ether glycol having a hydroxyl number of approx. 170 mg KOH/g with 700 parts (approx. 20-30% molar excess) of commercial soybean fatty acids. The mixture was purged with nitrogen and heated to 240° C. Water was removed overhead using the nitrogen purge (vacuum could optionally be applied). The esterification product was placed in a 2 liter flask equipped for vacuum distillation with a continuous stream sparge. The system was purged with nitrogen, sealed, evacuated to a pressure of <1 torr pressure and then heated to 240° C. Beginning at 200° C., steam was injected into the liquid product while excess free fatty acids were distilled overhead. After 3-4 hours, the residual acidity was reduced to approx. 0.3% (as oleic acid). The purified fatty acid-esterified polytetramethylene ether glycol (PTMEG-1) was a bland tasting oil with low odor which had the appearance of a conventional vegetable oil.

Using similar methods, additional esterified PTMEGs were also prepared starting with 1000 molecular weight polytetramethylene ether glycol (PTMEG-2) and 2900 molecular weight polytetramethylene ether glycol (PTMEG-3).

To measure the relative rate of enzyme-catalyzed hydrolysis, the esterified PTMEGs were challenged by porcine pancreatic lipase. Test emulsions were prepared using the aforementioned esterified PTMEGs according to the procedures described by Naher, "Lipase Titrimetric Assay", in *Methods in Enzymatic Analysis*, Vol. 2, 2nd Eng. ed., p. 814 (1974), except that the samples were not neutralized prior to generation of the emulsion. 20 mL samples of the esterified PTMEGs were utilized. The emulsions were generated in a Waring blender equipped with a stainless steel jacketed container (300 mL capacity). The jacketed blender container was filled with an ice-in-water suspension to cool the emulsion during preparation. Hydrolysis of the samples at pH 8.50 and two enzyme levels (200 and 4000 units/assay) was monitored via the automatic pH stat method described by Naher using a Radiometic Copenhagen RTS822 recording titration system (equipped with a PHM84 pH meter and a REA 270 derivatization unit) and a 0.1N sodium hydroxide solution. The enzymatic reactions were maintained at 37° C. under a nitrogen atmosphere.

The results obtained for the esterified PTMEGs prepared as described hereinabove and for olive oil and soybean oil controls are shown in Table I. The table also provides comparative data for an esterified alkoxylated polyol made by reacting 8 equivalents of propylene oxide with one equivalent of glycerin under basic conditions and esterifying with soybean fatty acids; this prior art fat substitute has a low (<5%) proportion of primary ester linkages. The results obtained demonstrate that the esterified PTMEG fat substitute of this invention is much more resistant towards lipase-catalyzed hydrolysis than olive oil or soybean oil, yet is more susceptible to such cleavage than an esterified alkoxylated polyol prepared in accordance with the teachings of U.S. Pat. No. 4,861,613. This finding was surprising in view of U.S. Pat. Nos. 5,059,443 and 5,077,073, which indicate that the rate of lipase-catalyzed hydrolysis is substantially independent of the structure of the ester linkages in an esterified alkoxylated polyol fat substitute. The high lipase resistance of the esterified PTMEGs was also unexpected in view of the fact that only 2 out of the 3 ester linkages in olive oil and soybean oil triglycerides are primary while in the esterified PTMEGs described herein all of the ester linkages are primary.

TABLE I

| Substrate | Hydrolysis Rate[a] | Hydrolyzability[b] | Normalized Hydrolyzability[c] |
|---|---|---|---|
| Esterified PTMEG-1 | 0.087 | 0.015 | 0.028 |
| Esterified PTMEG-2 | 0.055 | 0.008 | 0.020 |
| Esterified PTMEG-3 | 0.015 | 0.002 | 0.011 |
| Olive Oil | 3.26–7.62 | 1.00 | 1.00 |
| Soybean Oil | 3.62 | 0.738 | 0.723 |
| Esterified Propoxylated Glycerin | — | — | (0.001) |

[a] hydrolysis rate = #μ eq/min for an equivalent amount of enzyme
[b] relative to olive oil
[c] normalized hydrolyzability: hydrolyzability compared on an equal mmole basis (taking into account the concentration of ester linkages in a particular sample)

EXAMPLES 4–10

The procedure of Example 1 is repeated using the following fatty acid(s) in place of soybean oil fatty acids.

| EXAMPLE NO. | FATTY ACID |
|---|---|
| 4 | stearic acid |
| 5 | oleic acid |
| 6 | hydrogenated soybean oil fatty acids |
| 7 | corn oil fatty acids |
| 8 | cottonseed oil fatty acids |
| 9 | tallow fatty acids |
| 10 | coconut oil fatty acids |

EXAMPLES 11–20

The procedure of Example 1 is repeated using the following polytetramethylene ether glycols and fatty acids (in sufficient quantity such that at least 20% molar excess fatty acid is present relative to the hydroxyl number of the polytetramethylene ether glycol).

| EXAMPLE NO. | PTMEG HO(CH$_2$CH$_2$CH$_2$CH$_2$O)$_n$H  n = | FATTY ACID |
|---|---|---|
| 11 | 3 | hydrogenated high erucic rapeseed oil fatty acids |
| 12 | 10 | 50 parts peanut oil fatty acids/50 parts sallower oil fatty acids |
| 13 | 15 | behenic aid |
| 14 | 20 | lard fatty acids |
| 15 | 25 | olive oil fatty acids |
| 16 | 30 | canola oil fatty acids |
| 17 | 35 | palm oil fatty acids |
| 18 | 40 | partially hydrogenated soybean oil fatty acids |
| 19 | 45 | lauric acid |
| 20 | 50 | 3 parts behenic acid; 1 part lauric acid |

EXAMPLE 21

A trifunctional polytetramethylene ether glycol having 3 hydroxy groups per molecule and a molecular weight of 750 is prepared using the polymerization methods described in U.S. Pat. No. 4,728,722 (glycerin being utilized as the reactive hydrogen-containing compound in said method) and then esterified with excess partially hydrogenated corn oil fatty acids (iodine value=30) following the procedure of Example 1 to yield an esterified PTMEG useful as a reduced calorie fat substitute.

EXAMPLE 22

A hexafunctional polytetramethylene ether glycol having 6 hydroxy groups per molecule, a molecular weight of 1200, and a propylene oxide content of about 10% by weight (the oxypropylene units being present in a random manner within the polytetramethylene ether glycol rather than as an end block or cap) is prepared using the polymerization methods described in U.S. Pat. No. 4,728,722 (sorbitol being utilized as the reactive hydrogen-containing compound in said method) and then esterified with an excess of the following mixture of fatty acids: 2 parts by weight fully hydrogenated high erucic acid rapeseed oil fatty acids, 1 part by weight safflower oil fatty acids. The esterified PTMEG thereby obtained may be used as a full or partial replacement for a triglyceride lipid in the preparation of a food composition having reduced caloric content.

EXAMPLE 23

This example demonstrates the use of the esterified PTMEGs of this invention in the preparation of reduced calorie potato chips. A quantity of an esterified PTMEG obtained in the manner described in Example 2 sufficient to safely fill a 5 pound batch fryer is heated to a temperature of 365° F. (185° C.). Norchip potatoes which have been sliced to a thickness of about 0.052 inches (0.13 cm) are then submerged in the heated esterified PTMEG for a period of approximately 3 minutes or until the sliced potatoes achieve the desired degree of crispness and moisture content. The potato chips thus produced are then drained and seasoned. As a consequence of utilizing the esterified PTMEG, the available caloric value of the chips is significantly decreased relative to chips cooked in soybean oil, cottonseed oil, or peanut oil despite the fact that all of the ester linkages in the esterified PTMEG are primary in structure.

We claim:

1. A fat component useful for preparing a reduced calorie food product, said fat component comprising an edible triglyceride and a polytetramethylene ether glycol esterified with a fatty acid entity.

2. The fat component of claim 1 wherein the polytetramethylene ether glycol has a molecular weight of from 160 to 5000.

3. The fat component of claim 1 wherein the polytetramethylene ether glycol esterified with a fatty acid entity comprises at least 10% by weight of said fat component.

4. The fat component of claim 1 wherein the edible triglyceride is selected from the group consisting of tallow, soybean oil, cottonseed oil, coconut oil, palm kernel oil, corn oil, fish oil, lard, butter-fat, olive oil, palm oil, peanut oil, safflower seed oil, cocoa butter, sesame seed oil, rapeseed oil, sunflower seed oil, fully or partially hydrogenated derivatives thereof and mixtures thereof.

5. The fat component of claim 1 wherein the polytetramethylene ether glycol esterified with a fatty acid entity has an in-vitro normalized hydrolysis rate using porcine pancreatic lipase of greater than 1% and less than 20% of an olive oil standard.

6. The fat component of claim 1 wherein the polytetramethylene ether glycol esterified with a fatty acid entity has the general structure

wherein n is an integer of from 2 to 55 and $R^1$ and $R^2$ are the same or different and are $C_5$–$C_{23}$ paraffinic or olefinic groups.

7. The fat component of claim 1 wherein the polytetramethylene ether glycol has a functionality of from 1 to 8.

8. A fat component useful for preparing a reduced calorie food product, said fat component comprising an edible triglyceride and at least 25% by weight of a polytetramethylene ether glycol having a functionality of 2 and a molecular weight of from 400 to 3000 esterified with a $C_6$–$C_{24}$ fatty acid entity selected from the group consisting of caproic acid, enanthic acid, caprylic acid, pelargonic acid, decenoic acid, tetradecenoic acid, pentadecenoic acid, hexadecenoic acid, capric acid, lauric acid, elaidic acid, palmitic acid, stearic acid, oleic acid, cetoleic acid, myristic acid, linoleic acid, linolenic acid, eleostearic acid, eicosenoic acid, arachidonic acid, heptadecenoic acid, arachidic acid, behenic acid, erucic acid, lignoceric acid and halides, anhydrides, and esters thereof.

9. The fat component of claim 8 wherein the polytetramethylene ether glycol is completely esterified.

10. A reduced calorie food product comprised of at least one non-fat ingredient and a fat component, said fat component comprising a polytetramethylene ether glycol esterified with a fatty acid entity.

11. The reduced calorie food product of claim 10 wherein at least 25% by weight of the fat component is the polytetramethylene ether glycol esterified with a fatty acid entity.

12. The reduced calorie food product of claim 10 wherein the polytetramethylene ether glycol has a molecular weight of from 160 to 5000.

13. The reduced calorie food product of claim 10 wherein the polytetramethylene ether glycol esterified with a fatty acid entity has a caloric content of less than about 3 kilocalories per gram.

14. The reduced calorie food product of claim 10 wherein the non-fat ingredient is selected from the group consisting of proteins, carbohydrates, vitamins, and mixtures thereof.

15. The reduced calorie food product of claim 10 wherein the fat component is additionally comprised of a fat ingredient selected from edible triglycerides, esterified alkoxylated polyols, and polyol polyesters.

16. A reduced calorie food product comprised of at least one non-fat ingredient and a fat component, said fat component comprised of at least 25% by weight of a polytetramethylene ether glycol having a molecular weight of from 160 to 5000 esterified with a $C_6$–$C_{24}$ fatty acid entity.

17. The reduced calorie food product of claim 16 wherein the fat component consists essentially of the polytetramethylene ether glycol esterified with a $C_6$–$C_{24}$ fatty acid entity.

18. A method of reducing calories in a food product comprised of a fat component, where the method comprises replacing an effective portion of the fat component with a polytetramethylene ether glycol esterified with a fatty acid entity.

19. The method of claim 18 wherein the polytetramethylene ether glycol esterified with a fatty acid entity has the general structure

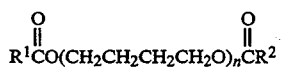

wherein n is from 4 to 40 and $R^1$ and $R^2$ are the same or different and are $C_5$–$C_{23}$ olefinic or paraffinic groups.

20. The method of claim 18 wherein at least 25 weight percent of the fat component is replaced with the polytetramethylene ether glycol esterified with a fatty acid entity.

21. The method of claim 18 wherein the fat component is additionally comprised of an edible triglyceride.

* * * * *